(12) United States Patent
Ollivier et al.

(10) Patent No.: US 6,197,999 B1
(45) Date of Patent: Mar. 6, 2001

(54) PHOTONITROSATION OF CYCLODODECANE IN CHLOROFORM IN QUASI-ANHYDROUS MEDIUM

(75) Inventors: Jean Ollivier, Arudy; Damien Drutel, Pau, both of (FR)

(73) Assignee: Atofina, Paris La Defense Cedex (FR)

( * ) Notice: Subject to any disclaimer, the term of this patent is extended or adjusted under 35 U.S.C. 154(b) by 0 days.

(21) Appl. No.: 09/446,975

(22) PCT Filed: Jul. 2, 1998

(86) PCT No.: PCT/FR98/01415

§ 371 Date: Apr. 17, 2000

§ 102(e) Date: Apr. 17, 2000

(87) PCT Pub. No.: WO99/01424

PCT Pub. Date: Jan. 14, 1999

(30) Foreign Application Priority Data

Jul. 2, 1997 (FR) .................................................. 97-08357

(51) Int. Cl.$^7$ .................................................. C07C 249/06
(52) U.S. Cl. ...................................... 564/253; 204/157.83

(58) Field of Search ........................ 564/253; 204/157.83

(56) References Cited

U.S. PATENT DOCUMENTS 3,853,729 * 12/1974 Lucas ........................... 204/162 XN
5,719,316 * 2/1998 Ollivier ............................... 564/253

FOREIGN PATENT DOCUMENTS

| 1240074 | 5/1967 | (DE) . |
| 0 798 290 | 10/1997 | (EP) . |
| 1095916 | 12/1967 | (GB) . |
| 1136747 | 12/1968 | (GB) . |

* cited by examiner

Primary Examiner—Peter O'Sullivan
(74) Attorney, Agent, or Firm—Millen, White, Zelano & Branigan, P.C.

(57) ABSTRACT

The invention relates to a process for the preparation of cyclododecanone oxide consists in photochemically reacting cyclododecane, dissolved in chloroform, a nitrosating agent and hydrogen chloride in a virtually anhydrous medium, that is to say under conditions such that the water content in the reaction medium does not exceed 1000 ppm.

12 Claims, No Drawings

PHOTONITROSATION OF CYCLODODECANE IN CHLOROFORM IN QUASI-ANHYDROUS MEDIUM

This application is a 371 of PCT/FR98/01415 filed Jul. 2, 1998.

The present invention relates to the field of polymers of the polyamide-12 type obtained by polymerization of lauryllactam. It more particularly relates to a process for the preparation of cyclododecanone oxime (reaction intermediate of lauryllactam) which consists in photonitrosating cyclododecane in chloroform in a virtually anhydrous medium.

The production of cycloaliphatic oximes by the photochemical route has been known for many years. Conventionally, a cycloalkane is reacted photochemically with a nitrosating agent, in particular nitrosyl chloride, in the presence of an excess of hydrogen chloride, at temperatures varying from −30° C. to +40° C. The oxime thus formed, in the hydrochloride form, is extracted from the reaction mixture, for example using a strong inorganic acid. This oxime is subsequently subjected to a rearrangement stage by the Beckmann reaction to form the corresponding lactam.

The production of lauryllactam in an industrial process under continuous operation is dependent on several limiting factors.

In the photonitrosation stage, the significant parameters directly related to the photochemical reaction are:
  the nature of the medium in which the cyclododecane is necessarily dissolved since the latter is solid at the normal reaction temperature (see, for example, DE-A-1,240,074 and GB-A-1,095,916),
  the nature of the solvent to be introduced into the reaction medium to increase the solubility of the oxime and thus to prevent its deposition on the wall of the irradiation lamps (see, for example, FR-A-1,335,823, FR-A-1,552,268 and GB-A-1,136,747), and
  the influence of the abovementioned solvents on the homogeneity and transparency of the reaction medium, which factors have a direct effect on the effectiveness of the light photons.

In the abovementioned state of the art, no reference is found to the influence of the water content in the reaction medium.

The Applicant Company has now found that the limitation of the water content in the industrial photonitrosation stage makes it possible to significantly increase the yield of cyclododecanone oxime and, consequently, to increase the profitability of the stages which are situated downstream, in particular the Beckmann rearrangement and the recycling of the acid used in the latter stage.

A subject-matter of the present invention is therefore a process for the preparation of cyclododecanone oxime which consists in photochemically reacting cyclododecane, dissolved in chloroform, a nitrosating agent and hydrogen chloride in a virtually anhydrous medium, that is to say under conditions such that the water content in the reaction medium does not exceed 1000 ppm.

The process according to the invention is carried out conventionally and under reaction conditions known for the photochemical nitrosation of cycloaliphatic compounds.

More specifically, in order to carry out the process according to the invention, cyclododecane is diluted in chloroform, the solution is saturated with gaseous hydrogen chloride, the nitrosating agent is added thereto and, finally, irradiation is carried out with light.

The moisture level in each reactant is chosen so that the overall water content in the reaction medium is between 50 and 1000 ppm and preferably 250 and 600 ppm.

The reaction is generally carried out in a reactor and the various reactants are introduced continuously.

The concentration of cyclododecane in the chloroform is generally between 0.1 and 35% by weight and preferably 20 and 30% by weight.

The nitrosating agent is generally chosen from nitrosyl chloride, a mixture of nitric oxide and of chlorine, or compounds capable of forming nitrosyl chloride in the reaction medium, for example alkyl nitrites which react with hydrogen chloride. Nitrosyl chloride is preferably used.

The addition of the nitrosating agent is adjusted so that its concentration in the reaction medium is between 0.1 and 25 g/l and preferably 1 and 2 g/l.

The hydrogen chloride is generally introduced in the form of an anhydrous gas, in excess with respect to the nitrosating agent. It is preferably employed at saturation of the cyclododecane solution.

Irradiation is carried out by means of one or more mercury or sodium vapour lamps emitting radiation with a wavelength of between 500 and 700 nm and preferably 565 and 620 nm.

The reaction is generally carried out at a temperature of between −20 and +40° C. and preferably +10 and +20° C.

The reaction is generally carried out with vigorous stirring, for example by means of one or more recirculation pumps.

The concentration of cyclododecanone oxime in the reaction medium should not generally exceed 15% by weight during the photonitrosation.

The irradiated reaction mixture is continuously withdrawn and it is extracted with a strong acid, preferably sulphuric acid having a concentration of greater than 80% by weight, at a temperature of between 10 and 50° C., preferably of the order of 20 to 25° C.

The cyclododecanone oxime thus formed is subsequently subjected to a Beckmann rearrangement stage in the presence of sulphuric acid in order to form lauryllactam.

The examples which follow make it possible to illustrate the invention.

EXAMPLE 1 a—Photonitrosation

A solution of cyclododecane in chloroform (450 g/l; 1 l/h), anhydrous gaseous hydrochloric acid to saturation and nitrosyl chloride are continuously introduced into a two liter (working volume) reactor equipped with a sodium vapour lamp having a power of 400 watts and emitting a radiation maximum in the vicinity of 595 nm. The nitrosyl chloride flow rate is adjusted so that the concentration in the reactor is maintained at 2 g/l of reaction medium. The water content in the reaction medium is 300 ppm.

The effluent gases emerging from the reactor are directed to a condenser (recovery of the solvent) and a sparger containing a sodium hydroxide solution (trapping of the hydrochloric acid).

The medium is continuously withdrawn at the rate of approximately 1.1 l/h.

Under stationary conditions, 0.63 mol/h or cyclododecanone oxime, 0.023 mol/h or monochlorocyclododecane, 0.0105 mol/h of chlorocyclododecanone oxime and 0.001 mol/h of dichlorocyclododecane are formed.

The number of moles of cyclododecane converted in one hour is 0.670.

The molar selectivity for cyclododecanone oxime is 0.94, calculated on the basis of the cyclododecane which has reacted.

Under these conditions, the hourly productivity of oxime is 1295 g/kW (optical pathlength of the lamp: 6.7 cm; energy efficiency=24%).

b—Beckmann rearrangement

The reaction medium withdrawn in stage a is treated with 98.5% sulphuric acid in order to extract the cyclododecanone oxime therefrom. After separation by settling, the recovered sulphuric solution comprises 36% by weight of the oxime.

200 g of the abovementioned sulphuric oxime solution are introduced over one hour into 100 g of 98.5% sulphuric acid maintained, with stirring, at 155° C. The mixture is subsequently brought to 160° C. for 30 minutes.

71.28 g of lauryllactam are recovered (molar yield: 99%).

The overall molar yield (photonitrosation+rearrangement) is 93%.

EXAMPLE 2 (COMPARATIVE)

a—Photonitrosation

The reaction is carried out under the conditions of Example 1, modified in that the solution of cyclododecane in chloroform comprises 2000 ppm of water. A portion of this water is kept in suspension in the solution by stirring in the device for mixing cyclododecane and chloroform situated upstream of the feed to the reactor.

In the stationary phase, 0.62 mol/h of cyclododecanone oxime, 0.0226 mol/h of monochlorocyclododecane, 0.0103 mol/h of chlorocyclododecanone oxime and 0.00098 mol/h of dichlorocyclododecane are formed.

The number of moles of cyclododecane converted in one hour is 0.667.

The molar yield of oxime is 0.929.

b—Beckmann rearrangement

The reaction is carried out under the conditions of Example 1. The sulphuric solution obtained after the extraction comprises 35% by weight of the oxime.

When the reaction is complete, 67.9 g of lauryllactam are recovered (molar yield: 97%).

The overall molar yield is 90.1%.

EXAMPLE 3 (COMPARATIVE)

a—Photonitrosation

The reaction is carried out under the conditions of Example 1, modified in that a 90% aqueous sulphuric acid solution is additionally introduced continuously into the reactor, so that the volume injected represents 10% of the total volume of the reaction medium.

The reaction medium continuously withdrawn is separated by settling. 0.43 mol/h of cyclododecanone oxime and 0.011 mol/h of chlorocyclododecanone oxime are recovered in the aqueous phase, and 0.016 mol/h of monochlorocyclododecane and 0.0005 mol/h of dichlorocyclododecane are recovered in the organic phase.

The number of moles of cyclododecane converted in one hour is 0.495.

The molar selectivity for cyclododecanone oxime is 0.875, calculated on the basis of the cyclododecane which has reacted.

Under these conditions, the hourly productivity of oxime is 890 g/kW.

b—Beckmann rearrangement

The reaction is carried out under the conditions of Example 1. The sulphuric solution obtained after the extraction comprises 30% by weight of the oxime.

On conclusion of the rearrangement, 68.4 g of lauryllactam are recovered (molar yield: 97%).

The overall molar yield is 84.8%.

What is claimed is:

1. A process for the preparation of cyclododecanone oxime comprising photochemically reacting cyclododecane, dissolved in chloroform, a nitrosating agent and hydrogen chloride under conditions such that the water content in the reaction medium does not exceed 1000 ppm.

2. A process according to claim 1, in which the water content is between 50 and 1000 ppm.

3. A process according to claim 2, in which the water content is between 250 and 6000 ppm.

4. A process according to claim 1, in which the nitrosating agent is nitrosyl chloride.

5. A process according to claim 1, in which the concentration of cyclododecane in the chloroform is between 0.1 and 35% by weight.

6. A process according to claim 1, in which the concentration of nitrosating agent is between 0.1 and 25 g/l of reaction medium.

7. A process according to claim 1, in which the hydrogen chloride is in excess with respect to the nitrosating agent.

8. A process according to claim 2, in which the nitrosating agent is nitrosyl chloride.

9. A process according to claim 8, in which the concentration of cyclododecane in the chloroform is between 0.1 and 35% by weight.

10. A process according to claim 9, in which the concentration of nitrosating agent is between 0.1 and 25 g/l of reaction medium.

11. A process according to claim 10, in which the hydrogen chloride is in excess with respect to the nitrosating agent.

12. A process according to claim 11, in which the water content is between 250 and 600 ppm.

* * * * *

UNITED STATES PATENT AND TRADEMARK OFFICE
CERTIFICATE OF CORRECTION

PATENT NO. : 6,197,999 B1
DATED : March 6, 2001
INVENTOR(S) : Ollivier et al.

It is certified that error appears in the above-identified patent and that said Letters Patent is hereby corrected as shown below:

ABSTRACT,
Line 2, delete "oxide" and replace with -- oxime which --

Column 4,
Claim 3, replace "6000" with -- 600 --.

Signed and Sealed this

Twenty-fifth Day of December, 2001

Attest:

Attesting Officer

JAMES E. ROGAN
Director of the United States Patent and Trademark Office